United States Patent [19]

Doran et al.

[11] Patent Number: 5,484,931
[45] Date of Patent: Jan. 16, 1996

[54] PROCESS FOR PREPARING FLUNIXIN AND INTERMEDIATES THEREOF

[75] Inventors: Henry J. Doran, Bray Co.; Donal J. Coveney, Dundrum, both of Ireland

[73] Assignee: Schering Corporation, Kenilworth, N.J.

[21] Appl. No.: 244,883

[22] Filed: Jun. 15, 1994

Related U.S. Application Data

[63] Continuation-in-part of Ser. No. 812,183, Dec. 20, 1991, abandoned.

[51] Int. Cl.$^6$ .................... C07D 213/26; C07C 233/07; C07C 209/00
[52] U.S. Cl. .................... 546/310; 564/218; 564/412; 564/414; 564/442
[58] Field of Search .................... 564/218, 412, 564/414, 442; 546/310

[56] References Cited

U.S. PATENT DOCUMENTS

| | | | |
|---|---|---|---|
| 3,337,570 | 8/1967 | Sherlock et al. | 260/295.5 |
| 3,390,172 | 6/1968 | Scherrer | 260/578 |
| 3,407,056 | 10/1968 | Schwartz | 564/218 |
| 3,839,344 | 10/1974 | Sherlock | 260/295.5 |
| 3,891,761 | 6/1975 | Sherlock | 424/266 |
| 4,081,451 | 3/1978 | Mayer | 260/295.5 |
| 4,132,737 | 1/1979 | Molloy | 260/578 |
| 4,172,095 | 10/1979 | Steinman | 260/578 |
| 4,209,464 | 6/1980 | Steinman et al. | 260/578 |
| 4,302,599 | 10/1981 | Peer et al. | 564/414 |
| 4,394,309 | 7/1983 | Stolzer | 564/414 |
| 5,248,781 | 9/1993 | McKillop | 546/310 |

FOREIGN PATENT DOCUMENTS

| | | | |
|---|---|---|---|
| 0295674 | 12/1988 | European Pat. Off. | |
| 5813194 | 8/1983 | Japan | 564/442 |
| 2194533 | 3/1988 | United Kingdom | |

OTHER PUBLICATIONS

Tamura, Y. et al., J. Org. Chem, 46 pp. 3564–3567 (1981).
Makosza, M. et al., J. Org. Chem. 49 pp. 1488–1494 (1984).
Marsais, F. et al., J. Chem. Soc. Perkins Trans. pp. 2611–2612 (1990).
Journal of Organic Chemistry, 1977, 42,3491.
Ho., P. T. Can. J. Chem. 1980, 58,861.
Yashimitzu Tamura, J. Org. Chem. 1981, 46, 3564.
Heinz W. Gschwend and Walton Fuhrer. J. Org. Chem., vol. 44, (1979), pp. 1133–1136.
J. M. Muchowski and M. Venuti, J. Org. Chem., vol. 45, pp. 4798–4801, 1980.

*Primary Examiner*—Shailendra Kumar
*Attorney, Agent, or Firm*—Joseph T. Majka; Edward H. Mazer

[57] ABSTRACT

Process for preparing a key intermediate, 2-methyl-3-trifluoromethylaniline (MTA) of Flunixin, as well as novel intermediates thereof are described.

6 Claims, No Drawings

PROCESS FOR PREPARING FLUNIXIN AND INTERMEDIATES THEREOF

The present application is the U.S. national application corresponding to International application No. PCT/US 92/10696, filed Dec. 16, 1992 and designating the United States, which PCT application is in turn a continuation-in-part of U.S. application Ser. No. 007/812,183, filed Dec. 20, 1991, now abandoned.

BACKGROUND

Flunixin, known as 2-[[2-methyl-3-(trifluoromethyl)-phenyl]amino]-3-pyridinecarboxylic acid, is a potent analgesic, particularly well suited for parenteral administration. The compound 2-methyl-3-trifluoromethylaniline (MTA) is a valuable intermediate for preparing flunixin, but is difficult to prepare due to the unique positioning of three different substituents in the 1-, 2- and 3- positions on the benzene ring. Heinz W. Gschwend and Walton Fuhrer, J. Org. Chore., Vol. 44, (1979), pp. 1133–1136 teach the specific ortho substitution of N-pivaloylanilines via the dilithio species with n-butyl lithium. J. M. Muchowski and M. Venuti, J. Org. Chore., Vol. 45, pp. 4798–4801 teach the ortho functionalization of N-t-butoxycarbonyl derivatives with tert-butyllithium and suggest that this group is more easily removed than the N-pivaloyl group. UK Patent Application 2194533 describes the preparation of 2-amino-6-trifluoromethyltoluene (i.e. 2-methyl-3-trifluoromethylaniline) from dichlorotrifluoromethyltoluene. It would be desirable to provide a process for preparing flunixin and its intermediate, MTA, in as few or even fewer steps than other processes previously taught. It would be desirable to provide novel intermediates which allow easy and convenient methylation ortho to nitrogen with little or no formation of undesirable by-products.

SUMMARY OF THE INVENTION

A process for preparing flunixin and pharmaceutically acceptable salts thereof, comprising:

a) methylating a compound of the formula (III):

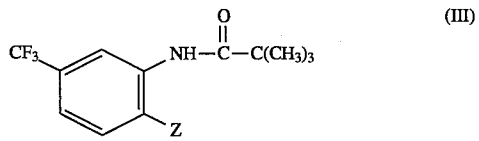

wherein, Z is hydrogen or a halo blocking group to give compound (V):

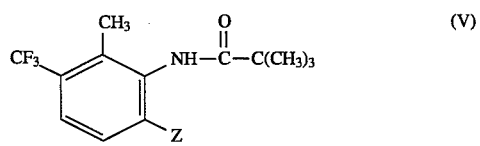

wherein Z is defined as before;

b) In a first alternative, for compounds of formula (V) wherein Z is a halo blocking group, contacting compound (V) with a reducing agent to give compound (VI):

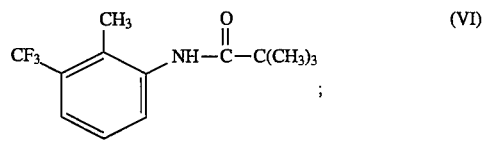

and hydrolyzing compound (VI) with acid to give 2-methyl-3-trifluoromethylaniline (MTA); or In a second alternative, for compounds of formula (V) wherein Z is a halo blocking group, hydrolyzing compound (V) with acid to give compound (VII):

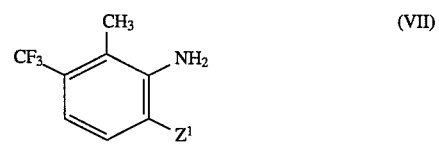

wherein $Z^1$ is a halo blocking group; and contacting compound (VII) with a reducing agent to give MTA; or In a third alternative, for compounds of formula (V) wherein Z is H, separating compound (VI) from the reaction mixture; and hydrolyzing compound (VI) with acid to give MTA; or In a fourth alternative, for compounds of formula (V) wherein Z is H, hydrolyzing the reaction mixture with acid; and from the reaction mixture, separating out MTA;

c) converting 2-methyl-3-trifluoromethylaniline (MTA) from any of the above alternatives in step b) to 2-[[2-methyl-3-(trifluoromethyl) phenyl]amino]-3-pyridinecarboxylic acid (flunixin) or pharmaceutically acceptable salts thereof.

Preferably, flunixin is prepared via the first or second alternatives (Routes A and B, respectively), most preferably via the first alternative route. Also preferred is that compound (III) wherein Z=halo blocking group is methylated using butyllithium and dimethylsulfate. In another embodiment, the present invention is directed toward a process for preparing a compound of the formula:

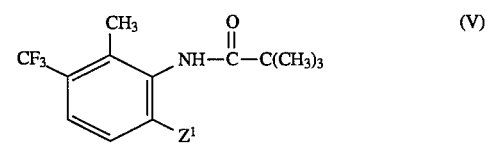

wherein $Z^1$ is a halo blocking group, comprising methylating a compound of the formula (111):

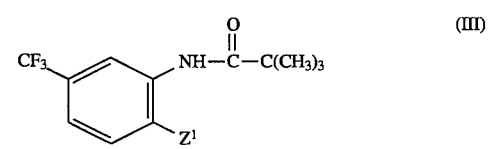

wherein $Z^1$ is as defined above, with an alkyl- or aryllithium reagent and a methylating electrophile to give compound (V). Preferably $Z^1$ is chloro, the alkyllithium reagent is butyllithium and the methylating electrophile is dimethylsulphate.

In another embodiment, the present invention is directed toward a process for preparing 2-methyl-3-trifluoromethylaniline (MTA) comprising hydrolyzing a compound of the formula:

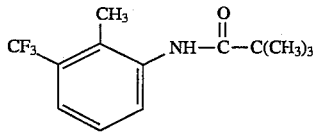
(VI)

with hydrogen bromide to give MTA. In yet another embodiment, the present invention is directed toward novel intermediates of the formula:

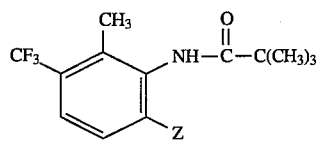
(V)

wherein Z is hydrogen or a halo blocking group. Preferably Z is chloro. The above intermediates are useful for the preparation of flunixin and pharmaceutical acceptable salts thereof. The present invention has the advantage of preparing flunixin and its intermediate, MTA, in as few or even fewer steps as other processes previously taught. The present invention also has the advantage of providing novel intermediates for preparing MTA, allowing easy and convenient preparation of MTA.

The present process and various alternative routes and embodiments thereof are illustrated as follows.

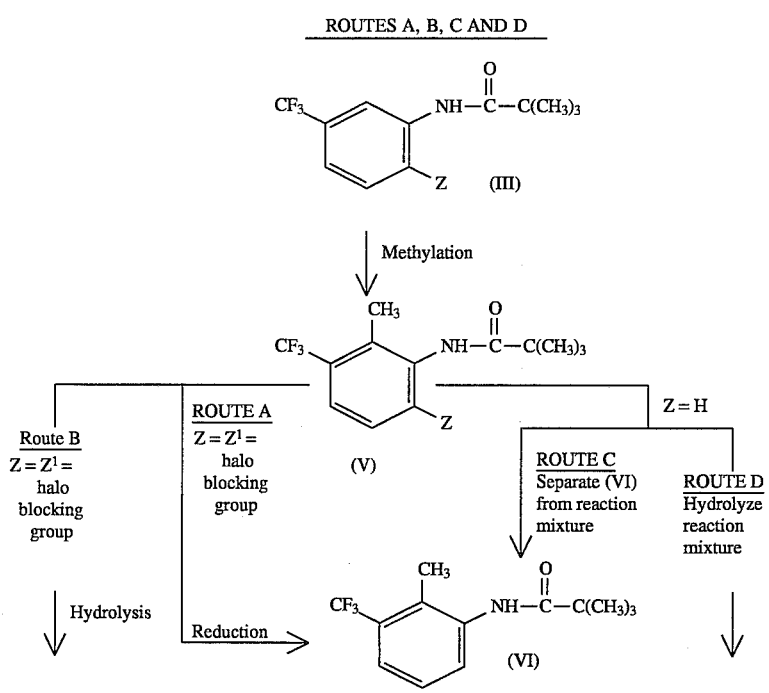

ROUTES A, B, C AND D

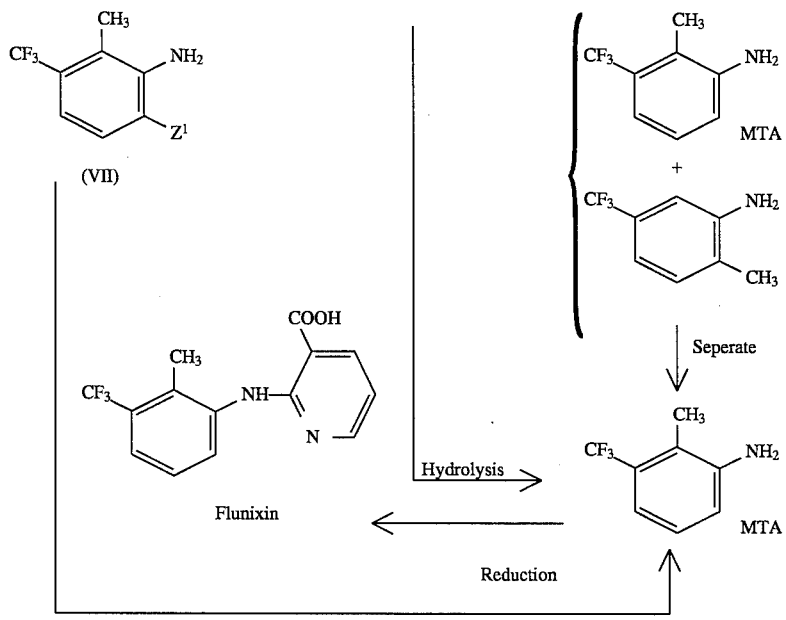

DETAILED DESCRIPTION OF THE EMBODIMENTS

The term "alkyllithium" refers to lithium reagents with one to ten carbon atoms in the alkyl portion, such as methyl, ethyl, propyl, butyl, hexyl and the like. Preferably the alkyllithium is a butyllithium, such as n-butyl, t-butyl or sec-butyl.

The term "aryllithium" refers to lithium reagents containing a benzenoid ring, such as phenyl.

The term "halo" refers to chloro, bromo, iodo or fluoro.

The term "methylating electrophile" refers to reagents of the formula $CH_3-X$ where X is any suitable anion leaving group, such as $CH_3OSO_3-$(dimethylsulfate), $CH_3SO_3-$, $CCl_3SO_3-$, $CF_3SO_3-$, $CH_3$-phenyl-$SO_3-$, phenyl-$SO_3-$, I-(methyl iodide), Br-(methyl bromide), Cl- and the like.

The term "halo blocking group" refers to any $Z=Z^1$ moiety on the benzene ring and which prevents methylation at that location on the ring but can be displaced by hydrogen under reducing conditions. Such halo blocking groups can include chloro, bromo, iodo and fluoro.

In Routes A, B, C and D, pivalanilide compound (V) can be prepared by methylating pivaloyl compound (III), via contacting pivaloyl compound (III) with alkyl- or aryllithium and a methylating electrophile with a solvent under conditions effective to give pivalanilide (V). The alkyl- or aryllithium reagent can be employed in amounts ranging from excess to about two moles alkyl- or aryllithium reagent per mole of compound (III), preferably from about 3 to about 2 moles alkyl- or aryllithium reagent, more preferably from about 2.2 to about 2.1 moles alkyl- or aryllithium reagent. The methylating electrophile can be employed in amounts ranging from excess to about equimolar amounts of methylating electrophile per mole of compound (III), preferably from about 2 to about equimolar amounts of methylating electrophile, more preferably about 1.0 to about 1.1 moles methylating electrophile. The reactants can be contacted at about a temperature ranging from about −25° C. to about 0° C., more preferably from about −25° C. to about −15° C.

In Route A, compound (VI), 2-methyl-3-trifluoromethylpivalanilide, can be prepared by contacting pivalanilide (V) wherein $Z=Z^1$ is a halo blocking group, with a reducing agent using catalytic hydrogenation or reduction using a formate salt with a catalyst. Where catalytic hydrogenation is employed, displacement of the halo blocking group with hydrogen can be carried out with a hydrogenating catalyst such as palladium charcoal in a C-1 to C-8 alcohol such as methanol. Hydrogenation is preferably carried out at about 35° C. and at pressures greater than ambient, preferably about 50 lbs pressure. A scavenger such as sodium acetate is used to tie up the protic acid of the displaced halo blocking group, i.e., HBr, HCl, HF or HI. The scavenger can be employed in amounts ranging from excess to about equimolar compared to one mole of the halo blocking group, preferably about 1.2 moles scavenger. Alternatively, compounds (VI) can be prepared by reduction of pivalanilide (V) in an alcohol solvent with a formate salt as described in Journal of Organic Chemistry, 1977, 42, 3491. Suitable salts include ammonium, sodium or triethylammonium formate. From compound (VI), 2-methyl-3-trifluoromethylaniline (MTA) can be prepared by hydrolyzing compound (VI) with a suitable acid under conditions effective to promote hydrolysis of the pivaloyl moiety (i.e., $-NHCOC(CH_3)_3$) to amino (i.e., $-NH_2$). Suitable acids include mineral acids such as sulfuric acid, hydrofluoric acid, hydrochloric acid, phosphoric acid, hydriodic acid and hydrobromic acid, preferably hydrobromic acid (hydrogen bromide or HBr). The acid can be employed in amounts ranging from excess to about equimolar amounts per mole of compound (VI), preferably from about 20 to about 4 moles acid, more preferably from about 4 to about 7 moles of acid per mole of compound (VI). The contacting of the reactants can be carded out at temperatures ranging from about 70° C. to the boiling point of the reaction mixture, preferably from about 90° C. to 150° C., more preferably from about 110° to 120° C.

In Route B, compound (VII) wherein $Z=Z^1$ is a halo blocking group can be prepared by hydrolysis of compound (V) with concentrated acids. Such concentrated acids can include strong organic acids such as alkyl or aryl sulfonic acids including methane sulfonic acid and paratoluene sulfonic acid. Other concentrated acids can include strong inorganic acids such as hydrochloric, sulfuric or phosphoric acid. Compound (VII) can be reduced to MTA using reducing conditions as described in Route A.

In Route C, compound (VI) wherein Z is hydrogen, is separated from a reaction mixture also containing 2-methyl-5-trifluoromethylpivalanilide, an undesirable isomer, using separatory procedures such as recrystallization from toluene, ethyl acetate or acetone. Compound (VI) can be hydrolyzed with acid to MTA using the procedures described in Route A.

In Route D, a reaction mixture containing compound (V) and the undesirable isomer 2-methyl-5-trifluoromethyl-pivalanilide is hydrolyzed with acid as described in Route A. Conventional recovery procedures such as fractional distillation are used to recover MTA from the reaction mixture.

MTA prepared from Routes A, B, C and D can be used to prepare flunixin by known methods, such as those described in U.S. Pat. Nos. 3,337,570; 3,839,344 and 3,891,761. Generally, MTA is contacted with 2-chloronicotinic acid in the presence of an acid catalyst, i.e., p-toluenesulfonic acid, followed by acidification Of the aqueous solution to give 2-[[2-methyl-3-(trifluoromethyl)phenyl]amino]-3-pyridinecarboxylic acid (flunixin). The meglumine salt of flunixin can be prepared by contacting flunixin with N-methyl-D-glucamine in a suitable solvent, such as isopropanol and collecting the precipitated product.

EXAMPLE 1

Preparation of MTA and Flunixin Meglumine via Route A.

i.) A solution of 2-chloro-5-trifluoromethylpivalanilide (70.0 g )in tetrahydrofuran (210 ml) is cooled to −25° C. under a nitrogen atmosphere. Then n-butyl lithium (345 ml, 1.6M in hexane, 2.2 equivalents) is added slowly at −25° C. After addition, the solution is warmed to −15° C. maintained at −15° C. for 2 hours and cooled to −25° C. Dimethyl sulphate (34.7 g, 1.1 equivalents) is added slowly at −20° C., the mixture is stirred for ten minutes and 140 ml of water are added. The mixture is heated to 50° C. and the layers are separated. The organic layer is washed with three 35 ml portions of water at 50° C. and then evaporated. The solid residue is crystallised from toluene to give 6-chloro-2-methyl-3-trifluoromethylpivalanilide (50.4 g, 69% yield), as needles, melting point (m.p.) 160.5 to 161° C.

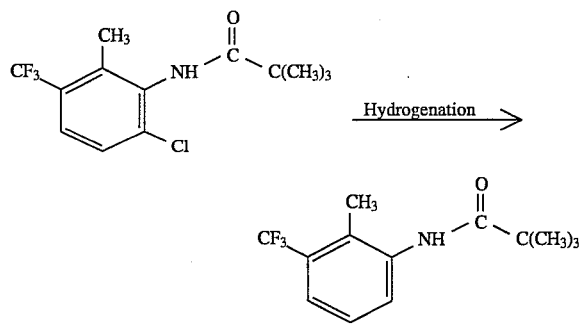

ii.) Palladium (5%) on charcoal catalyst (1.6 g)is added to a solution of 6-chloro-2-methyl-3-trifluoromethylpivalanilide (32.0 g) and sodium acetate (10.7 g, 1.2 equivalents)in methanol(130 ml). The mixture is hydrogenated at 50 p.s.i. (35,155 kg/m$^2$) at 35° C. for three hours. The catalyst is removed by filtration and the flitrate evaporated. The residue is dissolved in 100 ml of toluene and 50 ml of 2M aqueous NaOH with heating. The layers are separated and the toluene layer is washed with two 20 ml portions of water and evaporated. The residue is recrystallised from toluene to yield 27 g of 2-methyl-3-trifluoromethylpivalanilide (95% yield), as needles, mp 123.5°–125° C.

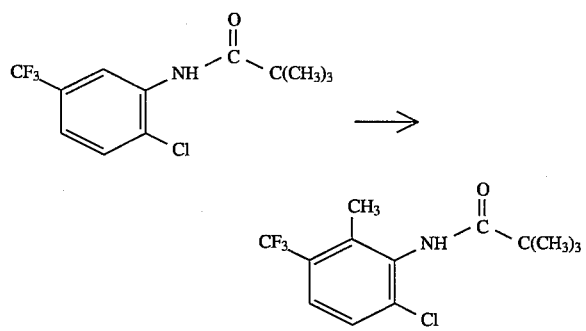

iii.) 2-methyl-3-trifluoromethylpivalanilide (10.0 g)is hydrolyzed by refluxing in concentrated HBr (40 ml, 48%) for 3 hours. The mixture is cooled to 20° C. and poured onto ice-water (40.0 g). The pH is adjusted to 9 with concentrated NaOH and the mixture is extracted with two. 30 ml portions of CH$_2$Cl$_2$. The CH$_2$Cl$_2$ extracts are dried over K$_2$CO$_3$ and evaporated to give 2-methyl-3-trifluoromethyl-aniline (MTA) (6.5 g, 96% yield), an oil which solidifies on standing.

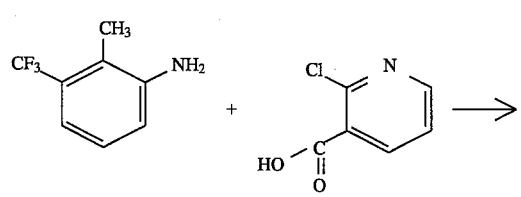

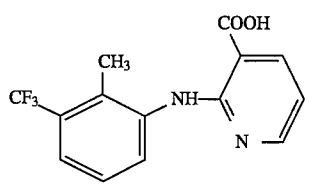

iv.) A mixture of 2-methyl-3-trifluoromethylaniline (368 g, 2.1 moles) and 2-chloronicotinic acid (158.0 g, 1.0 mole) in 400 ml of water is heated at 100° C. for 24 hours together with p-toluenesulfonic acid (15.0 g) monohydrate as the acid catalyst. Potassium hydroxide (ca. 145 g) in water (255 ml) is added and the pH is maintained above 11. After diluting the reaction mixture to 1.2 liters with water, the mixture is cooled to 50° C., adjusted to pH 11, treated with 7 g of a decolorizing charcoal and 15 g of a filter aid, and clarified by filtration. The flitrate is diluted with 750 ml of water and the pH is adjusted to 5.0 with concentrated sulfuric acid. Agitation of the suspension for 10 minutes and filtration gives crude, precipitated 2-[[2-methyl-3-(trifluoromethyl)phenyl]amino]-3-pyridinecarboxylic acid (flunixin) (83% yield). The compound can be further purified by crystallization in methanol and washing with water.

v.) Meglumine salt of Flunixin 2-[[2-methyl-3-(trifluoromethyl)phenyl]amino]-3-pyridinecarboxylic acid (296 g, 1.0 mole) and N-methyl-D-glucamine(201.0 g 1.03 moles) are dissolved in 2 liters of refluxing isopropanol. The heat is removed, 30 g of a decolorising carbon 15 g of a filter aid are added to the mixture, and the mixture is heated at reflux for 15 minutes. After clarification by filtration, the flitrate is agitated first at 45° C. until a precipitate forms and agitated again at 15° C. for one hour. The precipitate is filtered, washed with cord isopropanol and dried at 70° C. to give the meglumine salt of flunixin (95% yield).

EXAMPLE 2

Preparation of MTA via Route B.

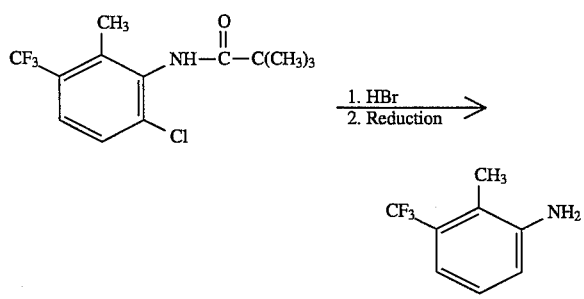

6-Chloro-2-methyl-3-trifluoromethylpivalanilide (150 g) is hydrolyzed by refluxing in concentrated HBr (48%, 700 ml) for 7 hours. The pH is adjusted to 9 with concentrated NaOH and the organic layer is separated and steam distilled to give 6-chloro-2-methyl-3-trifluoromethylaniline (76.3 g, 71%), an oil which solidifies on standing. Palladium (5%) on charcoal catalyst (2 g) is added to a solution of 6-chloro-2-methyl-3-trifluoromethylaniline (20 g) and sodium acetate (9.4 g, 1.2 equivalents)in methanol (100 ml). The mixture is hydrogenated at 50 psi at 25° C. for five hours. The catalyst is removed by filtration and the flitrate evaporated. The residue is dissolved in methyl t-butyl ether (60 ml) and 2M aqueous sodium hydroxide (20 ml) The layers are separated and the methyl t-butyl ether layer is washed with water (10 ml, twice), dried with K₂CO₃ and evaporated. The residue, 2-methyl-3-trifluoromethyl aniline (MTA) (15.8 g, 94%) solidifies on standing.

EXAMPLE 3

Preparation of MTA via Route C.

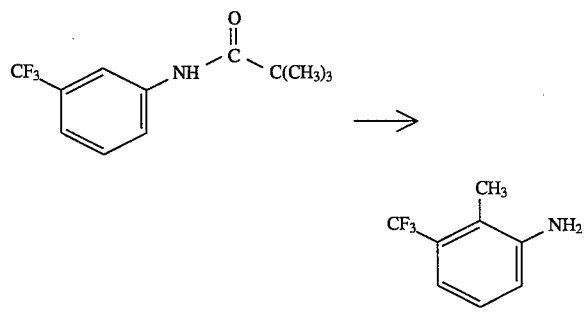

A solution of 3-trifluoromethylpivalanilide (9.8 g) in THF (40 ml) is cooled to −10° C. under a nitrogen atmosphere. n-Butyllithium (58 ml, 1.6M in hexane, 2.3 equivalents) is added slowly at −10° C. After addition, the solution becomes cloudy and the mixture is stirred at −2° C. for 2 hours, then cooled to −25° C. Dimethylsulphate (7.2 g, 1.4 equivalents) is added slowly at −20° C. After addition, the mixture is stirred at −20° C. for ten minutes and 40 ml of water and 10 ml of 25% ammonia are added. The mixture is warmed to room temperature and the layers are separated. The organic phase is washed with 20 ml of water, dried over K₂CO₃ and evaporated. Crystallization from acetone yields 5.6 g of off-white needles. Two recrystallizations from acetone yields 2-methyl-3-trifluoromethylpivalanilide (4.6 g, 44% yield), as needles, mp 123°–124° C. By using essentially the same procedure using HBr as described in Example 1, the 2-methyl-3-trifluoromethylpivalanilide is hydrolyzed to MTA.

EXAMPLE 4

Preparation of MTA via Route D.

The reaction mixture of Example 3 containing crude 2-methyl-3-trifluoromethylpivalanilide is hydrolyzed with HBr as described in Example 1. Fractional distillation under vacuum of the reaction mixture gives MTA.

PREPARATION OF STARTING MATERIALS

Starting material (III) used in the present process can be prepared according to the following scheme:

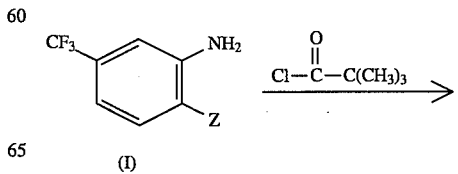

(I)

-continued

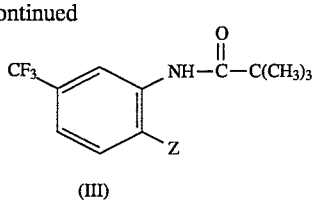

(III)

Essentially, a trifluoromethylaniline compound of formula (I) wherein Z is hydrogen or a halo blocking group, is contacted with t-butyl acid chloride or anhydride in the presence of a base and solvent to give compound (III), as described, for example, in Gschwend and Fuhrer, supra. Suitable bases include lithium carbonate, sodium carbonate, potassium carbonate, cesium carbonate, sodium hydroxide, potassium hydroxide and triethylamine. Suitable solvents include ethyl acetate, methylene chloride, acetone and toluene.

Preparative Example 1

2-chloro-5-trifluoromethyl pivalanilide

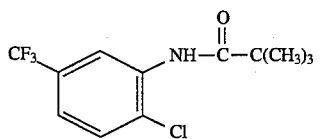

(III)

2-Chloro-5-trifluoromethylaniline (58.7 g) is dissolved in 180 ml of acetone and 47.7 g of sodium carbonate (1.5 equivalents) are added. Pivaloyl chloride (43.4 g, 1.2 equivalents) is added slowly to the stirred mixture and the mixture is cooled to a temperature below 30° C. After addition the mixture is stirred at room temperature for 6 hours. The acetone is removed under reduced pressure and the residue is dissolved in 300 ml of water and 180 ml of toluene. The mixture is heated to 70° C. for 15 minutes and the layers are separated. The toluene layer is washed with four 30 ml portions of water and evaporated under reduced pressure to give 82.4 g of the title compound (98% yield), an oil which solidifies on standing.

Preparative Example 2

3-Trifluoromethylpivalanilide

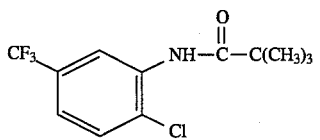

(III)

Pivaloyl chloride (40 g, 1.1 equivalents) is added slowly to a stirred mixture of 48.3 g of 3-trifluoromethylaniline (1.0 equivalents) and 35.0 g of sodium carbonate (1.1 equivalents) in 150 ml of ethylacetate. The mixture is cooled to a temperature below 30° C. After addition, the mixture is stirred at room temperature for one hour, 150 ml of water are added and the mixture is heated at 55° C. for 30 minutes. The layers are separated and the organic phase is dried over $K_2CO_3$ and evaporated. The solid residue is crystallised from isopropanol to yield 67.4 g of the title compound (92% yield), as needles, m.p 109.5°–110° C.

We claim:

1. A process for preparing 2-methyl-3-trifluoromethylaniline (MTA) comprising:

a) methylating a compound of the formula (III):

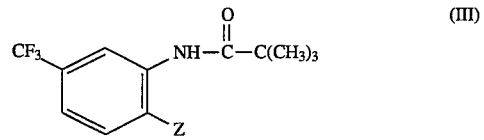

(III)

wherein Z is a halo blocking group to give compound (V):

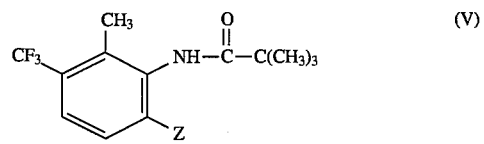

(V)

wherein Z is defined as before;

b) In a first alternative, for compounds of formula (V) wherein Z is a halo blocking group, contacting compound (V) with a reducing agent to give compound (VI):

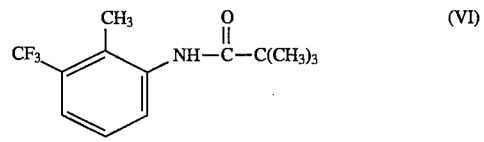

(VI)

and hydrolyzing compound (VI) with acid to give 2-methyl-3-trifluoromethylaniline (MTA); or In a second alternative, for compounds of formula (V) wherein Z is a halo blocking group, hydrolyzing compound (V) with acid to give compound (VII):

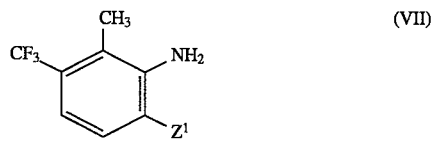

(VII)

wherein $Z^1$ is a halo blocking group; and contacting compound (VII) with a reducing agent to give MTA.

2. The process of claim 1 wherein compound (III) is methylated using butyllithium and dimethylsulfate and the acid is hydrogen bromide.

3. A process for preparing a compound of the formula:

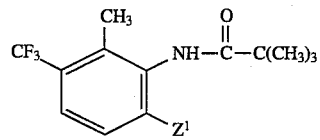

wherein $Z^1$ is a halo blocking group, comprising methylating a compound of the formula (III):

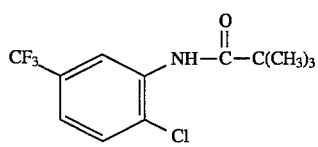

(III)

wherein $Z^1$ is as defined above, with an alkyl- or aryllithium reagent and a methylating electrophile to give compound (V).

4. The process of claim 3 wherein $Z^1$ is chloro, the alkyllithium reagent is butyllithium and the methylating electrophile is dimethylsulphate.

5. The process of claim 1 further comprising the step of contacting 2-methyl-3-trifluoromethylaniline (MTA) from claim 1 with 2-chloronicotinic acid in the presence of an acid catalyst, followed by acidification to give 2-[[2-methyl-3-(trifluoromethylphenyl]amino]-3-pyridinecarboxylic acid (flunixin).

6. A process for preparing flunixin and pharmaceutically acceptable salts thereof, comprising:

a) methylating a compound of the formula (III):

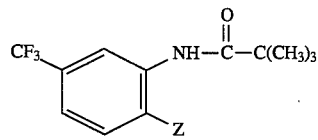

(III)

wherein Z is a halo blocking group to give compound (V):

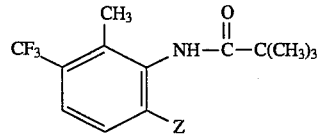

(V)

wherein Z is defined as before;

b) in a first alternative, for compounds of formula (V) wherein Z is a halo blocking group, contacting compound (V) with a reducing agent to give compound (VI):

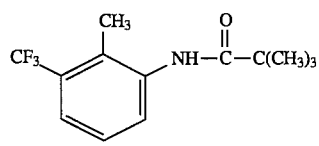

(VI)

and hydrolyzing compound (VI) with acid to give 2-methyl-3-trifluoromethylaniline (MTA); or In a second alternative, for compounds of formula (V) wherein Z is a halo blocking group, hydrolyzing compound (V) with acid to give compound (VII):

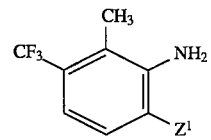

(VII)

wherein $Z^1$ is a halo blocking group;

and contacting compound (VII) with a reducing agent to give MTA;

c) contacting 2-methyl-3-trifluoromethylaniline (MTA) from either of the above alternatives in step (b) with 2-chloronicotinic acid in the presence of an acid catalyst, followed by acidification to produce 2-[[2-methyl-3-(trifluoromethyl)phenyl]amino]- 3-pyridinecarboxylic acid (flunixin) or pharmaceutically acceptable salts thereof.

\* \* \* \* \*